United States Patent
Brounstein

[19]

[11] Patent Number: 6,135,968
[45] Date of Patent: Oct. 24, 2000

[54] DIFFERENTIAL TEMPERATURE MEASURING DEVICE AND METHOD

[75] Inventor: Donald B. Brounstein, Summit, N.J.

[73] Assignee: Scantek Medical, Inc., Denville, N.J.

[21] Appl. No.: 08/926,790

[22] Filed: Sep. 10, 1997

[51] Int. Cl.[7] .................................................. A61B 5/103
[52] U.S. Cl. .......................................... 600/549; 600/587
[58] Field of Search .................................. 600/549, 555, 600/587, 595

[56] References Cited

U.S. PATENT DOCUMENTS

| | | |
|---|---|---|
| Re. 30,446 | 12/1980 | Meyers et al. . |
| Re. 32,000 | 10/1985 | Sagi . |
| 3,661,142 | 5/1972 | Flam . |
| 3,830,224 | 8/1974 | Vanzetti et al. . |
| 3,951,133 | 4/1976 | Reese ...................................... 600/549 |
| 4,189,942 | 2/1980 | Giezen et al. . |
| 4,190,058 | 2/1980 | Sagi . |
| 4,232,552 | 11/1980 | Hof et al. . |
| 4,403,653 | 9/1983 | Davidson . |
| 4,459,046 | 7/1984 | Spirg . |
| 4,524,778 | 6/1985 | Brown, Jr. et al. . |
| 4,651,749 | 3/1987 | Sagi . |
| 4,744,368 | 5/1988 | Young et al. . |
| 4,747,413 | 5/1988 | Bloch . |
| 4,952,033 | 8/1990 | Davis . |
| 5,088,500 | 2/1992 | Wedel et al. . |
| 5,284,147 | 2/1994 | Hanaoka et al. . |
| 5,335,669 | 8/1994 | Tihon et al. . |
| 5,401,100 | 3/1995 | Thackston et al. . |
| 5,404,881 | 4/1995 | Cathaud et al. . |
| 5,423,332 | 6/1995 | Zirps et al. . |
| 5,572,995 | 11/1996 | Rohrberg . |
| 5,598,846 | 2/1997 | Peszynski . |
| 5,732,711 | 3/1998 | Fitzpatrick et al. ..................... 600/549 |
| 5,830,159 | 11/1998 | Netta ........................................ 600/549 |

*Primary Examiner*—Cary O'Connor
*Assistant Examiner*—Pamela Wingood
*Attorney, Agent, or Firm*—Cooper & Dunham LLP

[57] ABSTRACT

A device and method for sensing temperatures at internal body locations non-surgically accessible only through body orifices is disclosed. The device is particularly useful in medical applications such as screening for cancer and other abnormal biological activity signaled by an increase in temperature at a selected site. As applied to prostate examinations, a device is provided which may be temporarily, adhesively affixed to a user's fingertip or to a mechanical probe. In the preferred embodiment, the device includes two temperature sensing elements which may include a plurality of chemical indicators. Each indicator changes color in response to detection of a predetermined particular temperature. When properly aligned and installed, the first element is located on the palmar surface of the fingertip while the second element is located on the dorsal surface of the fingertip. After an examination glove has been donned over the fingertip carrying the device, a prostate examination is performed during which the first element is brought into constant but brief contact with the prostate region and the second element is similarly, simultaneously brought into contact with a dermal surface opposing the prostate region. Upon withdrawal of the fingertip from the rectum and removal of the glove, the two temperature sensing elements may be visually examined in order to determine the temperatures detected by each one. A significant difference in observed temperatures indicates the possibility of abnormal biological activity and the need for further diagnostic or medical procedures.

42 Claims, 3 Drawing Sheets

DIFFERENTIAL TEMPERATURE MEASURING DEVICE AND METHOD

TECHNICAL FIELD

The subject invention relates generally to a device used to screen, detect and visually display comparative body temperatures on body surfaces within a predetermined range. The device is particularly useful in medical applications such as the detection of abnormalities in the human prostate gland.

BACKGROUND OF THE INVENTION

Prostate cancer is a leading cause of male mortality. Approximately 30,000 deaths per year can be traced to this cause in the United States alone. Consequently, various methods of detecting such cancers have been developed which include palpation through rectal examinations, a prostate specific antigen blood test and examination using a combination of various electronic devices and direct physical contact with the organ. However, each of these methods suffers from some type of shortcoming.

Palpation through digital rectal examination is the simplest, most inexpensive and fastest method of detection. Unfortunately, it is also the least reliable or accurate. It relies on the subjective judgment and experience of the examiner and cannot, in any event, accurately indicate the location or size of a tumor. Furthermore, by its reliance solely on the examiner's sense of touch, by definition it cannot detect deeply embedded or particularly small growths. It therefore fails as an effective early warning indicator.

These difficulties led to the development of various prostate examination devices incorporating electronic or electrically-driven components. For example, various patents disclose the use of ultrasound devices designed for placement on fingertips to be used in conjunction with digital rectal exams. Typical of these are the patents to Hansoka, et al. (U.S. Pat. No. 5,284,147) and Wedel, et al. (U.S. Pat. No. 5,088,500). This type of fingertip ultrasound examination has become popular in many other areas of medicine as disclosed in the patent to Peszynski (U.S. Pat. No. 5,598,846) where a fingertip ultrasound transducer is provided for viewing internal body parts during surgery. But one or more of the following problems are inherent with these devices. Either they are relatively costly, their use and interpretation of their results require a high level of examiner skill or the time necessary for the examination procedure is excessively long thereby further raising the cost of use.

Another examination tool routinely used in conjunction with digital rectal examinations is the prostate specific antigen blood test (PSA). However, studies have shown that this blood test provides an undesirably high level of both inaccurate positive readings (up to 25%) and inaccurate negative readings (up to 30%). As a result, some men who do not need treatment are subjected to needless invasive medical procedures while others remain uninformed of their true condition. It has been found that the number of false positive and negative readings from the PSA test can be significantly reduced if the prostate specific blood antigen reading is divided by the volume of the prostate. To this end, the patent to Zirps et al. (U.S. Pat. No. 5,423,332) discloses a fingertip probe which includes a device for automatically and operator-independently determining in vivo the mass of the prostate gland. Although this device represents a significant advancement of the art in this field, it still requires the use of relatively costly and complex transducer and monitoring equipment.

In the 1950's, it was discovered that the surface temperature of skin in the area of a malignant tumor exhibited a higher temperature than that expected were no disease present. Thus, by measuring body skin temperatures, it became possible to screen for the existence of abnormal body activity such as cancerous tumor growth. With the development of liquid crystals and methods of forming temperature responsive chemical substrates, contact thermometry became a reality along with its use in medical applications. Devices employing contact thermometry could sense and display temperature changes through indicators which changed colors, either permanently or temporarily, when placed in direct physical contact with a surface such as skin, reflecting a temperature at or near the point of contact. An abnormal reading would alert a user to the need for closer, more detailed examination of the region in question. However, the art in this area has been directed primarily at sensing and displaying temperatures on exterior skin surfaces. Thus, for example, the patent to Vanzetti et al. (U.S. Pat. No. 3,830,224) disclosed the placement of temperature responsive, color changing liquid crystals at various points in a brassiere for the purpose of detecting the existence of breast cancer, while the patent to Sagi (U.S. Re. 32,000) disclosed the use of radially arranged rows of temperature responsive indicators deposited on a disc for insertion into the breast-receiving cups of a brassiere for the same purpose.

There has been a failure to recognize that the same principle may apply to internal body organs. An abnormally high temperature at the surface of an internal organ when compared with surrounding tissue also indicates the likelihood of a medical problem. However, with regard to the prostate, the prior art has concentrated not on internal organ temperature measurement as a screening tool but rather on monitoring prostate temperature during hyperthermic prostate gland treatments after a problem has been found to exist. The patent to Cathaud et al. (U.S. Pat. No. 5,404,881) discloses one type of rectal probe used for this purpose, while the patent to Tihon et al. (U.S. Pat. No. 5,335,669) discloses another.

The applicability of contact thermometry to internal organ diagnosis has gone unrecognized. The prior art does not evidence an understanding of the advantages of diagnostic measurement of temperature in the prostate region as an early indicator of abnormalities. Furthermore, none of the prior art devices used in prostate examination provide a simultaneously simple, speedy, accurate and cost-effective solution to the prostate screening procedure.

SUMMARY OF THE INVENTION

The present invention relates to a self-contained device for detecting and displaying temperatures. It has particular utility as a tool for medical diagnosis in monitoring abnormal biological activity in internal body organs and tissue non-surgically accessible through body cavities such as the prostate gland, although it has uses in other fields as well. The device aids in screening for the existence of abnormal subsurface activity such as the growth of malignant tumors, neoplasms, infections and inflammations. After it has been affixed to a probe which can be either a user's fingertip or a mechanical implement, the device is inserted into the chosen body cavity, applied to the selected region and then removed. A quick visual check of colors displayed on the surface of the device enables the user to determine whether unusually high temperatures have been detected.

The preferred embodiment of the device includes a first heat sensor affixed to an insulative support which is itself removably affixed to the probe and is designed to be placed into physical contact with the region of interest. A second heat sensor is affixed to a second insulative support which is also removably affixed to the probe and which is designed to come into contact with the opposing wall of the respective body cavity. After a period of short contact with the desired body surfaces, the probe is removed from the chosen body cavity. Visual examination of the second heat sensor provides an indication of the background, normal temperature in the general region of use, while examination of the first heat sensor indicates the temperature in the specifically selected region. A significant difference in readings between the two heat sensors indicates the existence of a potential problem which calls for further testing or medical diagnostic procedures.

The device is designed to be placed on one end of a probe. In the case of a fingertip used as a probe as in the preferred embodiment, the device is initially oriented by positioning the surface onto which one heat sensor is mounted opposite the palmar surface of the fingertip. The surface supporting the second heat sensor is then oriented opposite the dorsal surface of the fingertip where the fingernail of the user is located. After activating adhesive areas on the device, for example, by removal of film, the device may be pulled downward over the fingertip of the user or the fingertip may be inserted into the device. Elastic bands affixed to the sides of the two supports partially expand during installation of the device and simultaneously cause the heat sensors and their supporting surfaces to deflect to conformably fit to the shape of the user's fingertip. Downward motion is halted when the end of the fingernail of the user encounters a top band connecting the two heat sensors. The activated adhesive materials hold the deformed surfaces supporting the heat sensors in place against the fingertip. A medical examination glove may then be donned covering the fingertip onto which the device has been attached. In the case of a prostate examination, the fingertip including the device is first inserted into the rectum permitting the prostate to be examined by palpation. The device is then left in physical contact with the prostate region for a short period and the finger is removed from the rectum. After removal of the glove, the device is examined to obtain the comparative, differential visual temperature readings described above.

It is a primary objective of this invention to provide a device for measuring and displaying temperatures of the walls of internal body surfaces and organs.

An additional objective of this invention is to provide a device for examining and indicating whether abnormal biological activity has occurred in an internal region non-surgically accessible only through a body cavity.

It is a further objective of this invention to indicate the likelihood of malignant growths in internal body organs and surfaces non-surgically accessible only through a body cavity.

It is yet another objective of this invention to provide an inexpensive, disposable device for detecting the existence of abnormal biological activity in internal body organs and surfaces.

It is still another objective of this invention to visually indicate a background temperature of an internal body region for comparison with a temperature at at least one selected nearby internal body location for the purposes of determining whether a significant temperature difference exists between these two regions.

Yet an additional objective of this invention is to provide a device which is self-conforming to the shape of a probe onto which it is affixed.

It is another objective of this invention is to provide a device which assumes the proper position for use when pulled onto a fingertip or mechanical probe and which resists dislodgment during use and thereafter.

Another objective of this invention is to provide a device for quickly and reliably displaying a range of temperatures of one or more internal body surfaces accessible through a body cavity by causing chemically sensitive indicators to change color upon exposure to particular temperatures.

Yet a further objective of this invention is to provide a method for determining at least one temperature on at least one wall of an internal body surface or organ which is non-surgically accessible through a body cavity.

BRIEF DESCRIPTION OF THE DRAWINGS

The foregoing and other objects, aspects and advantages of the invention will be better understood from the following detailed description of the invention with reference to the drawings, in which.

DESCRIPTION OF THE INVENTION

Figure 1:
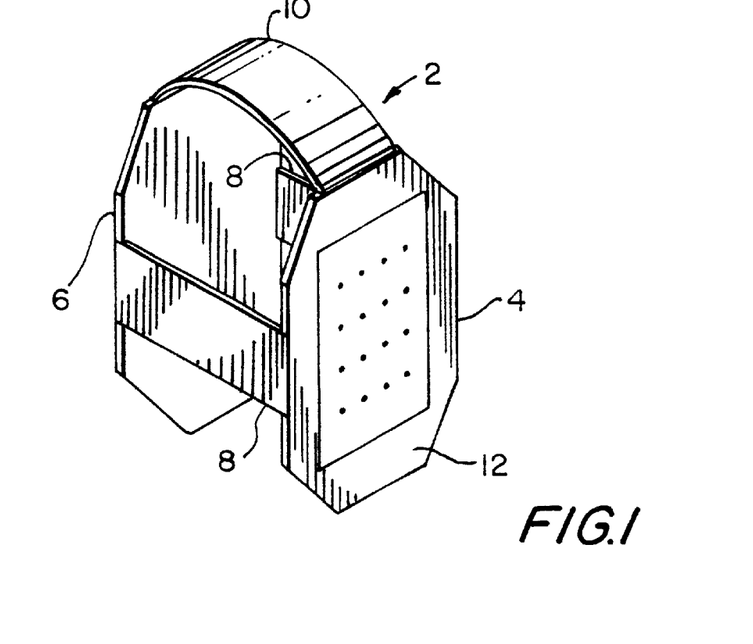
FIG. 1 is a perspective view of a preferred embodiment of the screening device of this invention used to sense and display temperature differentials at multiple locations measured inside a body cavity.

For a more detailed understanding of the invention, reference is first made to FIG. 1 of the drawings. This figure illustrates the preferred embodiment of screening device 2 of this invention which is particularly useful for sensing and displaying the surface temperatures of internal body organs and tissues in order to screen those regions for the existence of abnormal biological activity such as cancer. Although the following discussion is limited to application of the device of this invention to examination and screening of the prostate gland and nearby areas, the device can be equally well applied for use with any skin surface accessible through a body cavity in order to indicate, for example, abnormal polyp and neoplastic activity. Such surfaces may include, but are not limited to, rectal, vaginal and oral tissues. Even though some of these surfaces are at least partially, directly visible by the naked eye so that surface defects can be identified, lumps or tumors hidden under such surfaces can only be detected by other means such as those provided by this invention. The purpose of the device is not to provide definitive evidence of the existence of malignancies but rather to permit the user of the device to quickly and inexpensively monitor the surface temperature of one or more internal body organs or surfaces which are accessible in a body cavity without the need for invasive surgical procedures. The temperature display provided by this device alerts the user to the possibility of abnormal biological activity so that additional appropriate detailed medical testing and advice from health care professionals can be obtained in a timely and preventive fashion.

It is a medically accepted fact that skin surfaces in close proximity to malignancies, inflammations and infections exhibit higher temperatures than do surfaces where no abnormal biological activity is occurring. However, no simple, accurate and inexpensive device has been available to provide comparative temperature readings inside body cavities. The concept of differential temperature sensing in the rectal, colon and related gastrointestinal tract has great theoretical value since, for example, a differential temperature sensor could detect vascular abnormalities including early ulcerative conditions. Such a device would be an especially useful tool during standard prostate examinations since it would provide an additional indicium, besides physical palpation and the use of a PSA blood test, of abnormalities in the prostate gland.

Figure 2:
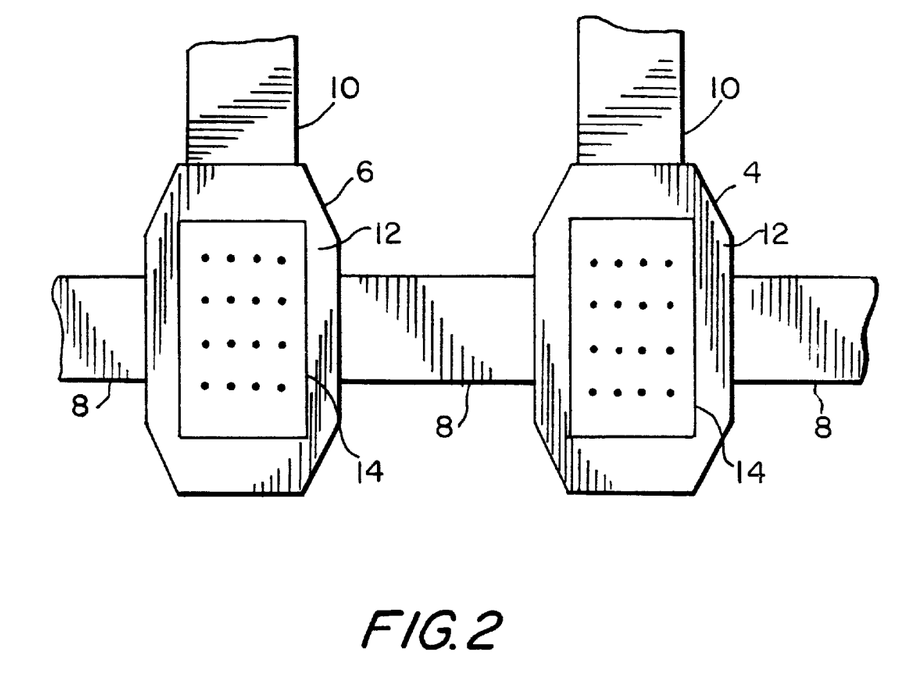
FIG. 2 is a planar view of the screening device of this invention.

Consequently, the preferred embodiment of this invention provides a screening device 2 which is designed to be affixed to a probe such as the gloved fingertip of a user and which enables measurement of the metabolic activity of the prostate gland relative to surrounding tissues. While other devices can measure core or ambient temperatures of the rectal area, this device is designed to select one region of interest and provide a differential temperature assessment of the selected region as compared to nearby tissue. Such an estimation can be useful in detecting metabolic tissue diseases and inflammation not only of the prostate but also of rectal tissue including polyps and other neoplastic locations. Screening device 2 is comprised of a palmar detector 4 and a dorsal detector 6, the sides of each of which may be attached to each other by means of horizontal band 8 and one end of each of which may be attached to each other by means of top band 10. A primary function of horizontal band 8 is to deflect palmar detector 4 and dorsal detector 6 into snug conformance with the contour of the user's fingertip while at the same time avoiding adverse affects on the blood circulation in that fingertip. Therefore, horizontal band 8 may be made from expandable, resilient, elastic materials such as urethane, synthetic latex, or rubber. In the preferred embodiment, horizontal band 8 may be two pieces of material, each of which connects the approximate middle of immediately adjacent sides of palmar detector 4 and dorsal detector 6. These two pieces of material may be integrated into palmar detector 4 and dorsal detector 6 as part of the manufacturing process or may be separately attached to each detector by an adhesive. Alternatively, horizontal band 8 may be a single, continuous loop of material which runs behind each of palmar detector 4 and dorsal detector 6 and is itself attached to each of them by any of a variety of adhesive means. In this alternative, horizontal band 8 would require the inclusion of adhesive means in order to affix each of the palmar detector 4 and dorsal detector 6 to the desired areas of the user's fingertip. Top band 10 connects adjacent ends of palmar detector 4 and dorsal detector 6 to each other. Primary functions of top band 10 include defining the proper vertical position of the device in relationship to the end of the user's fingertip and preventing further downward movement or dislodgment of device 2 after it has been properly positioned. Therefore, a flexible but less or non-expandable material, such as polyester, dacron or nylon, may be used in making top band 10. The bond between top band 10 and each of the detectors may be accomplished by means of thermal adhesion or use of a separate adhesive product or by integrating top band 10 into the detectors as part of the manufacturing process. The lengths of horizontal band 8 and top band 10 may be varied to accommodate different fingertip or probe sizes. In the case of a fingertip, for example, distal joint diameters of a middle finger onto which device 2 may be applied typically vary from approximately 1 to 2 centimeters. FIG. 2 depicts a flat, planar view of the preferred embodiment of screening device 2 in which horizontal band 8 and top band 10 have been graphically severed.

Figure 3:
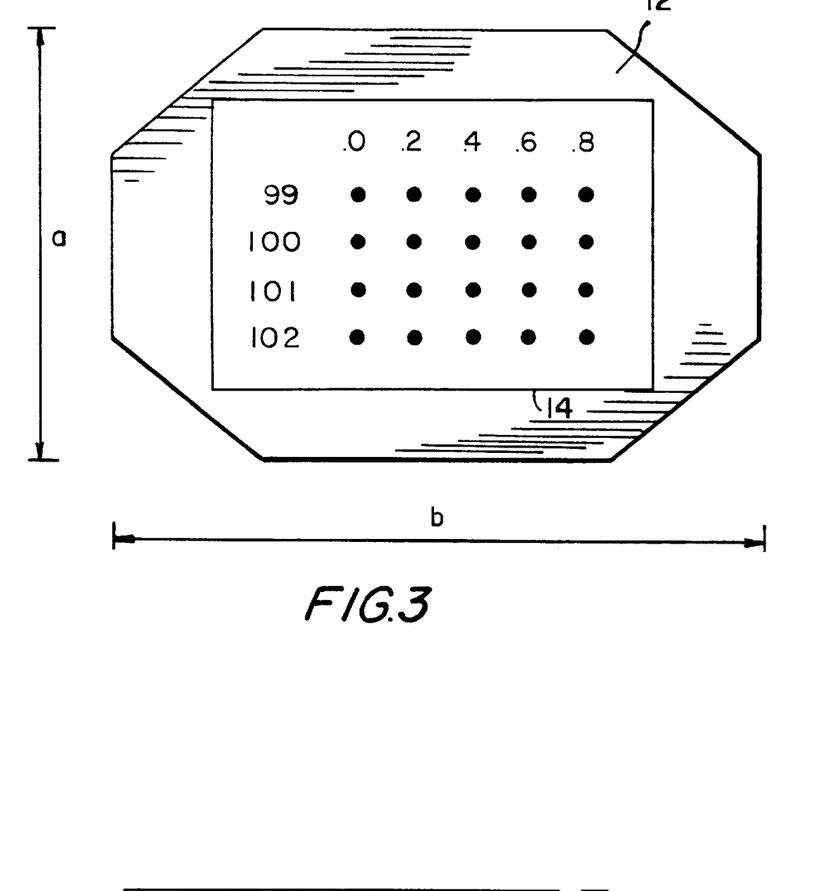
FIG. 3 is a planar view of a generic version of the palmar and dorsal detectors used in the preferred embodiment of the screening device of this invention.

FIG. 3 shows a generic planar view of palmar detector 4 and dorsal detector 6 which are similarly configured. In the preferred embodiment, each detector is comprised of support 12 having an inner surface and an outer surface. In the preferred embodiment, support 12 has a width a of approximately 0.85 centimeter and a length b of approximately 1.25 centimeters. Both the physical configuration and the dimensions a and b of support 12 can vary from those shown in FIG. 3 to meet the requirements of alternative embodiments and uses of the invention. It is also important to note that an important function of support 12 in all embodiments of the invention is to insulate temperature sensing patch 14 from the fingertip of the user and thereby improve the accuracy of the sensed temperatures by isolating temperature sensing patch 14 from the influence of heat emanating from the user's fingertip. Therefore, support 12 may be comprised of a closed cell polyurethane foam with a minimal thickness of, for example, from 1 to 2 millimeters. Such a material would be both pliable and insulative. Support 12 may include an adhesive area on the outer surface thereof to which a temperature sensing patch 14 is attached by means of adhesive material deposited either on the outer surface of support 12 itself or on the inner surface of the sensing patch. Temperature sensing patch 14 may be attached within the periphery of support 12 leaving a small amount of space between the edges of sensing patch 14 and the edge of support 12. In this configuration, space is provided in the periphery area for affixing both horizontal band 8 and top band 10 to support 12 and for permitting deflection of the sides of support 12 when it is brought into conformance with the contour of the user's fingertip as explained below. However, it would also be possible to enlarge sensing patch 14 to encompass the entire surface of support 12 by adhesively affixing horizontal band 8 and top band 10 to the inner surface of support 12. Both support 12 and temperature sensing patch 14 are formed of a flexible, pliant material. These features are desirable in order to assure that screening device 2 adheres and conforms to its user's fingertip when compressively attached thereto, as described below. The inner surface of support 12 may include an adhesive material. In the preferred embodiment, this adhesive is meant to bind the inner surface of support 12 of palmar detector 4 to the exterior of the palmar surface of a fingertip of a user and the inner surface of support 12 of dorsal detector 6 to the fingernail area of the fingertip of a user. This is possible if an adhesive covering or layer such as PIB (polyisobutylene) or a similar adhesive seal material designed with a minimally aggressive adhesive mixture is applied along with a removable protective film to the inner surface of support 12 for each detector so that screening device 2 will be held in place after removal of the glove. To further ensure a stable, precise fit, a similar adhesive may also be applied to the inner surface of horizontal band 8 which is in contact with the skin of the user after screening device 2 is placed into position. Finally, yet additional stability may be provided by applying a similar adhesive to the inner surface of top band 10 which is in contact with the skin of the user after screening device 2 is placed into position. The material of the glove will have either no or a minimal effect on the transmission of temperature to palmar detector 4 and, in any event, whatever effect there is will impact both palmar detector 4 and dorsal detector 6 equally, thereby maintaining the relative accuracy and meaningfulness of the differential temperature measuring aspects of the invention. In a first alternative embodiment, however, it is possible to affix support 12 directly to the exterior surface of a glove-covered finger of a user. In a second alternative embodiment, screening device 2 may be incorporated into a chosen fingertip of a specially designed medical examination glove made from latex or another suitable material. In a third alternative embodiment, screening device 2 can be affixed directly to an appropriately sized mechanical probe thereby dispensing with the need for an examination glove.

Figure 4:
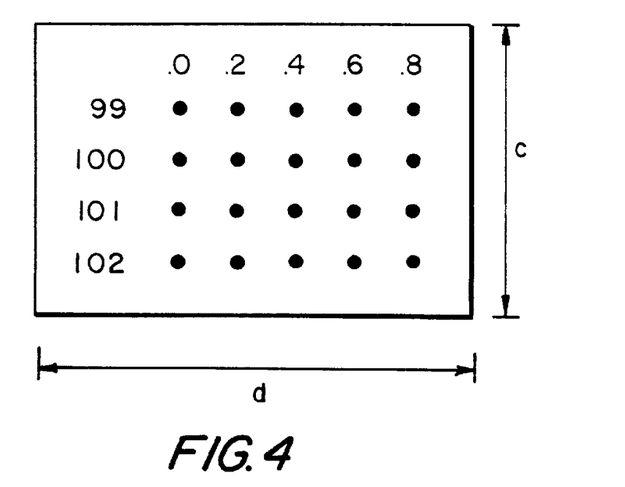
FIG. 4 is a planar view of the temperature sensing patch of this invention.
Figure 5A:
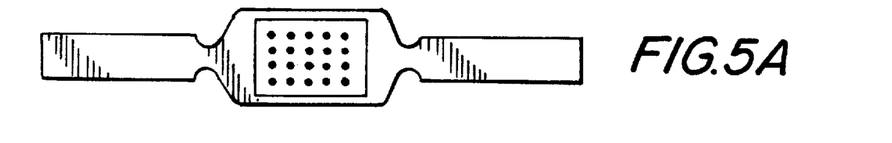
FIGS. 5A through 5D illustrate frontal, planar views of various other configurations of the screening device of this invention.
Figure 5B:
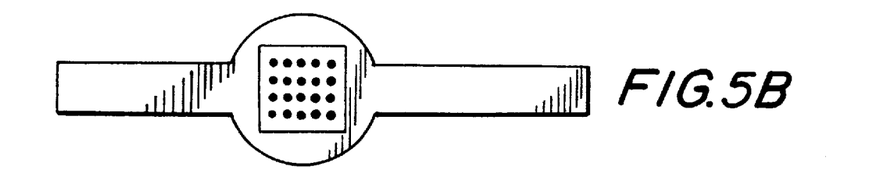
Figure 5C:
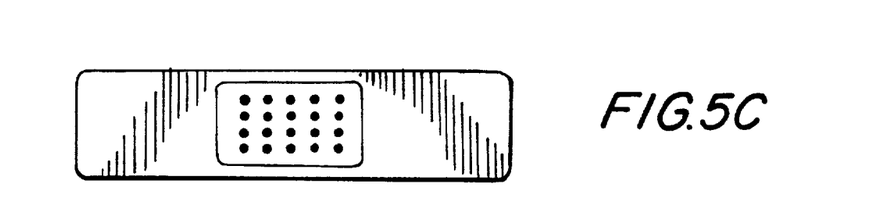
Figure 5D:
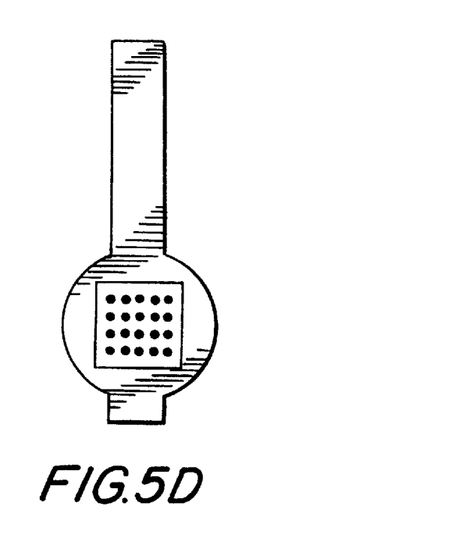

FIG. 4 shows a planar view of temperature sensing patch 14 which is comprised of a group of equally spaced-apart parallel rows of temperature sensitive chemical indicators deposited on a heat transmissive material. The indicators melt and change color when exposed to specific predetermined, different temperatures thereby displaying the temperature to which they have been exposed and enabling a visual reading thereof. The indicators may be comprised of a layer of encapsulated cholesteric liquid crystals, ortho-bromonitrobenzine, ortho-chloronitrobenzine or materials such as those described in the patent to Hof, et al. (U.S. Pat. No. 4,232,552), although a variety of other materials may also be used. In the preferred embodiment, sensing patch 14 has a width c of approximately 0.65 centimeters and length d of approximately 1.05 centimeters, although these dimensions may be varied. The heat transmissive material may be a woven mesh of highly thermally conductive material such as silver, copper or gold, the use of which enhances the efficiency of heat transmission by reducing the thickness and surface area across which thermal energy must be transferred to reach the indicators. The use of a woven mesh also increases the malleability and conformability of sensing patch 14 which, as described below, is a desirable feature for purposes of this invention. An alternative type of sensing patch which can also be used in this invention employs a conductive foil as the heat transmissive material upon which temperature sensitive chemical indicators are deposited. In still another alternative type of sensing patch, the temperature sensitive indicators can be replaced by digital temperature sensors or fiber type material including but not limited to optical fiber which can also record temperatures accurately and quickly. Temperature sensing patch 14 of this invention differs from that discussed above in that it employs far fewer temperature sensitive chemical indicators and is designed to measure a narrower thermal range. Thus, in the preferred embodiment, there are only 20 indicators. A range of 99° F. to 102° F. can be measured wherein indicators within each horizontal row, reading down vertically, correspond to a full degree F. increment in temperature and indicators within each column, reading across from the left vertically, correspond to a two tenths degree F. increment in temperature. The numbers appearing adjacent the rows and columns of indicators on temperature sensing patch 14 in FIG. 4 provide a visual numeric guide to the sensed temperatures and facilitate reading of the results from use of the device. These numbers may be omitted, if so desired. By altering the size of temperature sensing patch 14 or of the spacing between the indicators, either more or fewer indicators could be included on the sensing patch and the range could be either increased or decreased. Once the indicators are deposited onto the heat transmissive material, they are sealed in place and the heat transmissive material is bonded to support 12 by application of a transparent cover layer such as a pressure sensitive polyisobutylene adhesive seal. An example of a suitable cover layer of this type is disclosed in the patent to Giezen, et al. (U.S. Pat. No. 4,189,942). In still another alternative embodiment of temperature sensing patch 14, the need to use a heat transmissive material as a substrate onto which the temperature sensitive chemical indicators are deposited could be eliminated by replacing that material with a soft, pliable substrate, such as polymer film, silicone or latex. Since the films used in the laminating structure of device 2 are extremely thin, such a substitution would only result in minor loss of thermal conductivity as compared with a heat transmissive material which would not be detrimental to the performance of device 2.

FIGS. 5A through 5D illustrate frontal, planar views of various other configurations of screening device 2. These alternative arrangements are not to be considered exclusive as many other possibilities exist. The embodiments of FIGS. 5A, 5B and 5C rely on only a version of horizontal band 8 to retain screening device 2 in place while FIG. 5D relies only on a version of top band 10 for this function. The preferred embodiment, however, provides greater stability by employing both horizontal band(s) 8 and top band 10. The alternative embodiments of FIGS. 5A through 5D may employ either two detectors or a single palmar detector. Although embodiments of the single detector type would forego the added benefits of providing differential temperature readings, they would still provide a device for simple, accurate and speedy measurement of direct, absolute internal body surface temperatures. Furthermore, in the case of a single detector, either a single horizontal band 8 attached to opposing sides of support 12 could be used to cause support 12 to conform to the user's fingertip and to retain the device in place or such a single horizontal band 8 in conjunction with an appropriately sized top band 10 interconnecting the middle of horizontal band 8 with the middle of the top end of support 12 could be used for these purposes. In the case of the embodiment of FIG. 5D, deflection of support 12 could be caused manually and the deformation retained by the use of a temporary adhesive. Moreover, still other embodiments of this invention could include more than two detectors, for example, providing left and right lateral detectors or multiple detectors longitudinally displaced along the length of the probe on the same or multiple sides of the device which would provide even more detailed, separate differential temperature readings. In the case of multiple detectors, the number and configuration of horizontal bands 8 would have to be adjusted accordingly as would the arrangement of one or more top bands 10. It is also possible to make various sizes of screening device 2 in order to accommodate different fingertip sizes. In cases where screening device 2 is incorporated into a glove, the glove would itself be made available in various sizes. Yet another embodiment of device 2 would replace the need for horizontal band 8 and top band 10 with a fingertip or partial to full finger-length covering made from an elastic, resilient material into which one or more detectors could be incorporated or onto which such detectors could be adhesively applied.

In order to obtain a temperature measurement, the user takes an appropriately sized version of screening device 2 prior to a rectal examination and removes any protective films, as required, covering adhesive areas of the inner surfaces of the support(s) 12, horizontal band(s) 8 and top band 10. The device is then oriented so that the inner surface of top band 10 directly opposes and runs approximately perpendicularly across the center of the edge of the fingernail of the chosen probing finger onto which screening device 2 is to be applied and palmar detector 4 is on the palmar side of that same finger and centered over that area.

Figure 6:
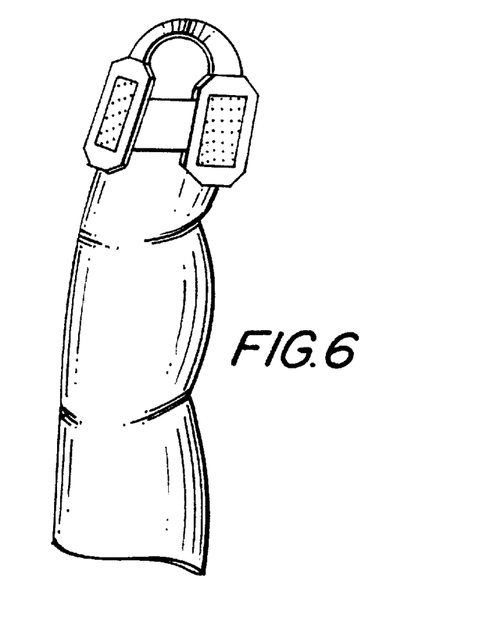
FIG. 6 is a perspective view of a finger onto the tip of which the screening device of this invention has been applied.

Screening device 2 is then installed onto the user's fingertip by either pulling or pushing it firmly onto the fingertip of the desired finger or inserting the fingertip therein until all of the inner surface of top band 10 comes into firm contact with the fingernail and skin of the fingertip and the adjacent ends of palmar detector 4 and dorsal detector 6 are approximately parallel to each other on opposite sides of the user's fingertip. The elastic action of horizontal band(s) 8 will draw the edges of both palmar detector 4 and dorsal detector 6 towards each other causing each detector to deflect and conform to the shape of the fingertip. The adhesive materials will then cause the inner surface of support 12 of palmar detector 4 to adhere to the external skin surface of the user's finger and the inner surface of dorsal detector 6 to adhere to the external surface of the fingernail of the user's finger. FIG. 6 provides a perspective view of a fingertip with a screening device 2 installed thereon. The user then dons a latex or synthetic medical grade examination glove by pulling the glove over the hand including the fingertip on which screening device 2 has been installed. The importance of top band 10 then becomes apparent since it acts to resist the downward deflection experienced by screening device 2 while donning the glove. The same resistive principle applies if an alternative embodiment were used in which screening device 2 is incorporated into a glove fingertip. Upon donning the glove, the user would insert the probing finger through the anus and palpate the prostate or other region of interest. Once palpation has been completed, the user would place gentle pressure on the target site and hold the outer surface of temperature sensing patch 14 in contact with the target site preferably for approximately 15 seconds, although the minimum time required could vary depending on the particular type of temperature sensing materials chosen. Due to the size of the rectal cavity, while palmar detector 4 is held in contact with the region of interest, the temperature sensing patch 14 of dorsal detector 6 would inherently be in physical contact with a biological surface opposing the region of interest. Following the 15 second dwell time, the finger is withdrawn from the body, the glove could be removed and discarded without danger of dislodging screening device 2 due to the adhesive materials and the displayed results could be immediately read. This procedure may be aesthetically preferable from the viewpoint of the user when reviewing results of the screening process as opposed to reading screening device 2 when it is either incorporated into a glove or separately attached to a previously glove-covered finger. Palmar detector 4 would display the temperature in the region of interest, while dorsal detector 6 would indicate the general systemic, background temperature. The difference between the two temperature readings would be recorded as the thermal variation. Thermal variation exceeding a normal level would be considered an abnormal finding and would call for further diagnostic procedures. This variation may theoretically range from 1° F. to several degrees F. depending on a variety of factors including the patient's general health and the type of condition being diagnosed.

Although various elements in the previously described embodiments of this invention have been disclosed with reference to particular types of materials, it should be understood that the functions performed by these materials may also be performed in appropriate cases by other types of materials and that this invention is not limited by reference to the specific materials disclosed. Furthermore, the embodiments described above are not to be construed as the only possible implementations of this invention. Other embodiments are possible so long as the functions described above are properly performed.

What is claimed is:

1. A device for placement on a probe such as the fingertip of a user for measuring and displaying a range of temperatures on internal body surfaces after being placed into physical contact therewith comprising:

at least two flexible heat sensing means for providing comparative measurements and displays of the temperatures of internal body surfaces brought into physical contact with each of said heat sensing means wherein each of said heat sensing means is comprised of a plurality of equally spaced-apart parallel rows of temperature sensing indicators;

at least two flexible support means for insulating each of said heat sensing means from the probe, one of said heat sensing means being mounted on each of said flexible support means; and attachment means for causing the device to conform to the contour of the probe and for removably affixing the device to the probe.

2. The device of claim 1 wherein each temperature sensing indicator is comprised of a chemical substance having a first color which melts upon exposure to a specified temperature and assumes a second color.

3. The device of claim 2 wherein said temperature sensing indicators are deposited onto a thermally conductive material.

4. The device of claim 3, wherein the thermally conductive material has a top surface and a bottom surface and wherein the bottom surface thereof includes adhesive material.

5. The device of claim 1, wherein each temperature sensing indicator is digitally based.

6. The device of claim 1, wherein each temperature sensing indicator is fiber based.

7. The device of claim 1, wherein each said support means is a closed cell of polyurethane foam.

8. The device of claim 7, wherein each said support means has a thickness of between 1 and 2 millimeters.

9. The device of claim 1, wherein said attachment means further comprises:

horizontal band means for interconnecting adjacent sides of each of said support means and for causing each of said support means to be drawn into conformable physical contact with the surface of the probe; and adhesive means for causing each of said support means to become removably attached to the probe.

10. The device of claim 9, wherein said horizontal band means is comprised of an elastic material.

11. The device of claim 10, wherein the elastic material is urethane, synthetic latex, or rubber.

12. The device of claim 9, wherein said horizontal band means is comprised of a number of separate parts equal to the number of said flexible support means and wherein each part connects adjacent sides of two of said flexible support means.

13. The device of claim 9, wherein said horizontal band means is a single loop of elastic material interconnecting all of said flexible support means and includes an adhesive for removably affixing the material to the probe.

14. The device of claim 9, wherein said attachment means further comprises top band means for defining the proper vertical positioning of the device when it is placed on a probe and for limiting the downward movement of the device after it is properly positioned.

15. The device of claim 14, wherein said top band means is comprised of a flexible, minimally expandable material.

16. The device of claim 15, wherein said top band means is polyester, dacron or nylon.

17. The device of claim 14, wherein said top band means interconnects the top ends of each of said flexible support means.

18. The device of claim 1, wherein the device is incorporated into a medical grade examination glove.

19. The device of claim 1, wherein there are two said flexible support means, one of said flexible support means being removably attached to the palmar surface of the probe and the other of said flexible support means being removably attached to the dorsal surface of the probe.

20. A device for placement on a probe such as the fingertip of a user for measuring temperatures within a designated range on a single internal body surface after being placed in physical contact therewith comprising:

flexible heat sensing means for measuring the temperature of an internal body surface brought into physical contact therewith wherein said heat sensing means is comprised of an array of equally spaced-apart parallel rows and columns of temperature sensing indicators;

flexible support means for insulating said heat sensing means from the probe, said heat sensing means being mounted on said flexible support means; and attachment means for causing the device to conform to the contour of the probe and for removably affixing the device to the probe.

21. The device of claim 20, wherein each temperature sensing indicator is comprised of a chemical substance having a first color which melts upon exposure to a specified temperature and assumes a second color.

22. The device of claim 21, wherein said temperature sensing indicators are deposited onto a thermally conductive material.

23. The device of claim 22, wherein the thermally conductive material has a top surface and a bottom surface and wherein the bottom surface thereof includes adhesive material.

24. The device of claim 20, wherein each temperature sensing indicator is digitally based.

25. The device of claim 20, wherein each temperature sensing indicator is fiber based.

26. The device of claim 22 wherein said support means is a closed cell of polyurethane foam.

27. The device of claim 26, wherein said support means has a thickness of between 1 and 2 millimeters.

28. The device of claim 20, wherein said attachment means further comprises:

horizontal band means for interconnecting the sides of said support means and for causing said support means to be drawn into conformable physical contact with the surface of the probe; and adhesive means for causing said support means to become removably attached to the probe.

29. The device of claim 28, wherein said horizontal band means is a single loop of elastic material.

30. The device of claim 29, wherein the elastic material is urethane, synthetic latex, or rubber.

31. The device of claim 28, wherein said attachment means further comprises top band means for defining the proper vertical positioning of the device when it is placed on a probe and for limiting the downward movement of the device after it is properly positioned.

32. The device of claim 31, wherein said top band means is comprised of a flexible, minimally expandable material.

33. The device of claim 32, wherein said top band means is polyester, dacron or nylon.

34. The device of claim 31, wherein said top band means interconnects one end of said support means with said horizontal band means.

35. The device of claim 20, wherein the device is incorporated into a medical grade examination glove.

36. A device for placement on a probe such as the fingertip of a user for measuring and displaying a range of temperature on internal body surfaces after being placed into physical contact therewith comprising:

at least one flexible heat sensing means for providing comparative measurements and displays of the temperatures of internal body surfaces brought into physical contact with said heat sensing means wherein said heat sensing means is comprised of a plurality of equally spaced-apart parallel rows of temperature sensing indicators deposited onto a thermally conductive material wherein each said temperature sensing indicator is further comprised of a chemical substance having a first color which melts upon exposure to a specified temperature and assumes a second color;

at least one flexible support means for insulating said heat sensing means from the probe, said heat sensing means being mounted on said flexible support means; and attachment means for causing the device to conform to the contour of the probe and for removably affixing the device to the probe.

37. The device of claim 36, wherein said support means is a closed cell of polyurethane foam having a thickness of between 1 and 2 millimeters.

38. The device of claim 36, wherein said attachment means further comprises:

horizontal band means comprised of an elastic material for interconnecting adjacent sides of said support means and for causing said support means to be drawn into conformable physical contact with the surface of the probe; and adhesive means for causing said support means to become removably attached to the probe.

39. The device of claim 38, wherein said attachment means further comprises flexible, minimally expandable top band means for defining the proper vertical positioning of the device when it is placed on a probe and for limiting the downward movement of the device after it is properly positioned.

40. A method for screening for abnormal biological activity in the vicinity of a selected internal body surface accessible through a body cavity by sensing and comparing the temperature sensed at such selected internal body surface with at least one temperature sensed at at least one nearby internal body surface through use of a screening device worn on a selected fingertip of a user, the device having at least two flexible, deformable heat sensing patches each of which is mounted on the outside surface of a separate flexible, deformable support comprising the steps of:

installing the device by either inserting the selected fingertip into the device or moving the device onto the selected fingertip until further movement is prevented and the supports are approximately parallel to each other;

donning a medical grade examination glove over the selected fingertip;

inserting the selected fingertip into the body cavity;

bringing the palmar area of the selected fingertip into direct physical contact with the selected internal body surface;

withdrawing the selected fingertip from the body cavity after a period of time sufficient to detect temperature change has elapsed;

removing the medical grade examination glove;

comparing the temperatures sensed by the heat sensing patches by assessing the colors of the indicators to determine if a significant difference exists between the temperature sensed by the heat sensing patch on the first support and the temperature sensed by any other heat sensing patch.

41. A method for screening for abnormal biological activity in the vicinity of a selected internal body surface accessible through a body cavity by sensing and comparing the temperature sensed at such selected internal body surface with an expected normal temperature through use of a screening device worn on a selected fingertip of a user, the device having a flexible, deformable heat sensing patch wherein the heat sensing patch is mounted on the outside surface of a flexible, deformable support comprising the steps of:

orienting the screening device so that the support is approximately centered over the palmar surface of the selected fingertip;

installing the device by either inserting the selected fingertip into the device or moving the device onto the selected fingertip until further movement is prevented and the original orientation is maintained;

deforming the support into conformable, removable, adhesive attachment with the surface of the selected fingertip;

donning a medical grade examination glove over the selected fingertip;

inserting the selected fingertip into the body cavity;

bringing the palmar area of the selected fingertip into direct physical contact with the selected internal body surface;

withdrawing the selected fingertip from the body cavity after a period of time sufficient to detect temperature change has elapsed;

removing the medical grade examination glove;

comparing the temperature sensed by the heat sensing patch by assessing the colors of the indicators to determine if a significant difference exists between the temperature sensed by the heat sensing patch on the support and the expected normal temperature.

42. A method for screening for abnormal biological activity in the vicinity of a selected internal body surface accessible through a body cavity by sensing and comparing the temperature sensed at such selected internal body surface with at least one temperature sensed at at least one nearby internal body surface through use of a screening device worn on a selected fingertip of a user, the device having at least two flexible, deformable heat sensing patches each of which is mounted on the outside surface of a separate flexible, deformable support having an inside surface with a protected adhesive area, an outside surface, two sides and two ends wherein the supports are attached to each other on adjacent sides by at least one elastic horizontal band and on one end by a relatively inelastic top band comprising the steps of:

donning a medical grade examination glove over the selected fingertip;

orienting the screening device so that the top band runs approximately perpendicularly across the middle of the fingernail of the selected finger and a first support is approximately centered over the palmar surface of the selected fingertip;

activating the adhesive areas on the inside surfaces of all of the supports by removing their protection;

installing the device by either inserting the selected, glove-covered fingertip into the device or moving the device onto the selected fingertip until the top band prevents further movement and the supports are approximately parallel to each other while maintaining the original orientation;

permitting the elastic action of the horizontal band to deform the supports into conformable, removable, adhesive attachment with the glove-covered surface of the selected fingertip;

inserting the selected fingertip into the body cavity;

bringing the palmar area of the selected fingertip into direct physical contact with the selected internal body surface;

withdrawing the selected fingertip from the body cavity after a period of time sufficient to detect temperature change has elapsed; and comparing the temperatures sensed by the heat sensing patches by assessing the colors of the indicators to determine if a significant difference exists between the temperature sensed by the heat sensing patch on the first support and the temperature sensed by any other heat sensing patch.

* * * * *